US009770187B2

United States Patent
Umeda et al.

(10) Patent No.: US 9,770,187 B2
(45) Date of Patent: Sep. 26, 2017

(54) MAGNETIC RESONANCE IMAGING APPARATUS

(71) Applicant: Toshiba Medical Systems Corporation, Otawara-shi (JP)

(72) Inventors: Masaaki Umeda, Sakura (JP); Satoshi Sugiura, Otawara (JP); Naoyuki Furudate, Otawara (JP); Hiroshi Kusahara, Nasushiobara (JP); Masaaki Nagashima, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 210 days.

(21) Appl. No.: 14/861,393

(22) Filed: Sep. 22, 2015

(65) Prior Publication Data

US 2016/0093047 A1 Mar. 31, 2016

(30) Foreign Application Priority Data

Sep. 30, 2014 (JP) .................................. 201-201910

(51) Int. Cl.
*A61B 5/055* (2006.01)
*A61B 5/00* (2006.01)
*G01R 33/483* (2006.01)

(52) U.S. Cl.
CPC ............ *A61B 5/055* (2013.01); *A61B 5/7214* (2013.01); *G01R 33/4835* (2013.01); *G01R 33/4838* (2013.01)

(58) Field of Classification Search
CPC .. A61B 5/055; A61B 5/7214; G01R 33/4835; G01R 33/4838

USPC .......................................................... 382/131
See application file for complete search history.

(56) References Cited

U.S. PATENT DOCUMENTS 7,054,675 B2 5/2006 Ma et al.
2013/0006094 A1* 1/2013 Charles .................. A61B 5/055
600/411

FOREIGN PATENT DOCUMENTS

JP 05-076516 3/1993
JP 05-154133 6/1993

* cited by examiner

*Primary Examiner* — Amandeep Saini
(74) *Attorney, Agent, or Firm* — Oblon, McClelland, Maier & Neustadt, L.L.P.

(57) ABSTRACT

A magnetic resonance imaging apparatus according to an embodiment includes a controller and a generator. The controller divides a plurality of slice regions that are sequentially arranged into a first group including two non-sequential slice regions and a second group including a slice region positioned between the two non-sequential slice regions and acquires data from the slice regions for each of the groups. When acquiring data from at least one of the two non-sequential slice regions, the controller acquires the data after applying a pre-sat pulse to a position between the two non-sequential slice regions. When acquiring data from the slice region positioned between the two non-sequential slice regions, the controller acquires the data after applying a pre-sat pulse to a position of at least one of the two non-sequential slice regions.

6 Claims, 5 Drawing Sheets

MAGNETIC RESONANCE IMAGING APPARATUS

CROSS-REFERENCE TO RELATED APPLICATIONS

This application is based upon and claims the benefit of priority from Japanese Patent Application No. 2014-201910, filed on Sep. 30, 2014; the entire contents of which are incorporated herein by reference.

FIELD

Embodiments described herein relate generally to a magnetic resonance imaging apparatus.

BACKGROUND

Conventionally, to perform an imaging process using a magnetic resonance imaging apparatus, a method is known by which pre-saturation pulses (hereinafter, "pre-sat pulses") to make fluid signals void are applied to the outside of an imaging region, for the purpose of inhibiting flow artifacts caused by fluids (e.g., blood, cerebrospinal fluid, etc.) flowing into the imaging region. For example, to acquire images of a plurality of slice regions that are sequentially arranged, a pre-sat pulse is applied to the outside of a region that collectively encloses all of the slice regions therein.

DETAILED DESCRIPTION

A Magnetic Resonance Imaging (MRI) apparatus according to an embodiment includes a controller and a generator. The controller is configured to divide a plurality of slice regions that are sequentially arranged into a first group including two non-sequential slice regions and a second group including a slice region positioned between the two non-sequential slice regions and to acquire data from the slice regions for each of the groups. The generator is configured to generate images of the plurality of slice regions on the basis of the data acquired by the controller. Further, when acquiring data from at least one of the two non-sequential slice regions, the controller acquires the data after applying a pre-sat pulse to a position between the two non-sequential slice regions. When acquiring data from the slice region positioned between the two non-sequential slice regions, the controller acquires the data after applying a pre-sat pulse to a position of at least one of the two non-sequential slice regions.

Exemplary embodiments of the MRI apparatus will be explained in detail below, with reference to the accompanying drawings.

Figure 1:
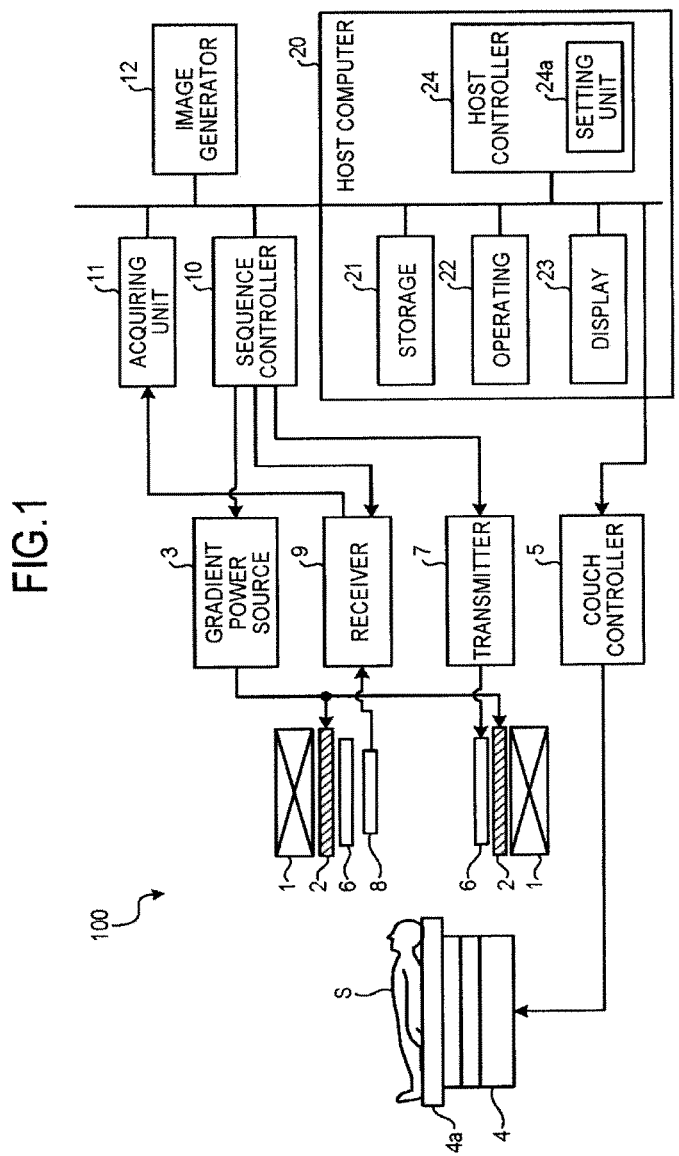
FIG. 1 is a block diagram of an exemplary configuration of a Magnetic Resonance Imaging (MRI) apparatus according to an embodiment.

FIG. 1 is a diagram of an exemplary configuration of an MRI apparatus according to an embodiment. For example, as illustrated in FIG. 1, an MRI apparatus 100 includes a magnetostatic field magnet 1, a gradient coil 2, a gradient power source 3, a couch 4, a couch controller 5, a transmitting coil 6, a transmitter 7, a receiving coil 8, a receiver 9, a sequence controller 10, an acquiring unit 11, an image generator 12, and a host computer 20.

The magnetostatic field magnet 1 is formed substantially in the shape of a hollow circular cylinder (which may have an oval cross-section orthogonal to the central axis thereof) and is configured to generate a uniform magnetostatic field in an imaging space that is formed on the inside thereof. The magnetostatic field magnet 1 may be configured by using, for example, a permanent magnet, a superconductive magnet, or the like.

The gradient coil 2 is formed substantially in the shape of a hollow circular cylinder (which may have an oval cross-section orthogonal to the central axis thereof) and is disposed on the inside of the magnetostatic field magnet 1. More specifically, the gradient coil 2 is structured by combining three coils corresponding to x-, y-, and z-axes that are orthogonal to one another. By using an electric current supplied from the gradient power source 3 to the three coils individually, the three coils generate, in the imaging space, gradient magnetic fields of which the magnetic field intensities change along the x-, y-, and z-axes that are orthogonal to one another. The z-axis direction is arranged to be the same as the direction of the magnetic flux of the magnetostatic field.

The gradient power source 3 causes the gradient coil 2 to generate the gradient magnetic fields by supplying electric power to the gradient coil 2. More specifically, the gradient power source 3 causes the gradient magnetic fields formed along a read-out direction, a phase-encoding direction, and a slice direction that are orthogonal to one another to be generated in the imaging space, by supplying the electric current individually to each of the three coils included in the gradient coil 2 and causing the gradient magnetic fields to be generated, as appropriate, along the x-, y- and z-axes. In the following explanations, the gradient magnetic field formed along the read-out direction will be referred to as a "read-out gradient magnetic field", the gradient magnetic field formed along the phase-encoding direction will be referred to as a "phase-encoding gradient magnetic field", and the gradient magnetic field formed along the slice direction will be referred to as a "slice gradient magnetic field".

These three directions are used for the purpose of appending spatial position information to Magnetic Resonance (MR) signals. More specifically, in the read-out gradient magnetic field, position information in the read-out direction is appended to Magnetic Resonance (MR) signals by varying the frequency of the MR signals in accordance with positions in the read-out direction. In the phase-encoding gradient magnetic field, position information in the phase-encoding direction is appended to MR signals, by varying the phase of the MR signals along the phase-encoding direction. In the slice gradient magnetic field, if the imaging region is a slice region, the slice gradient magnetic field is used for the purpose of determining the direction, the thickness, and the quantity of the slice regions, whereas if the imaging region is a volume region, position information along the slice direction is appended to MR signals by varying the phase of the MR signals in accordance with positions in the slice direction.

The couch 4 includes a couchtop 4a on which an examined subject (hereinafter, a "patient") S is placed. The couchtop 4a is inserted into the imaging space formed on the inside of the magnetostatic field magnet 1 and the gradient coil 2. For example, the couch 4 is provided so that the longitudinal direction thereof extends parallel to the central axis of the magnetostatic field magnet 1.

The couch controller 5 is configured to control operations of the couch 4. For example, by controlling a driving mechanism included in the couch 4, the couch controller 5 moves the couchtop 4a in longitudinal directions, up-and-down directions, and left-and-right directions.

The transmitting coil 6 is formed substantially in the shape of a hollow circular cylinder (which may have an oval cross-section orthogonal to the central axis thereof) and is disposed on the inside of the gradient coil 2. Further, the transmitting coil 6 is configured to apply a Radio Frequency (RF) magnetic field to the imaging space by using an RF pulse current supplied by the transmitter 7.

The transmitter 7 is configured to supply the RF pulse current corresponding to a Larmor frequency to the transmitting coil 6.

The receiving coil 8 is attached to the patient S placed in the imaging space and is configured to receive the MR signals emitted from the patient S due to the influence of the RF magnetic field applied by the transmitting coil 6. Further, the receiving coil 8 is configured to output the received MR signals to the receiver 9. For example, as the receiving coil 8, an exclusive-use coil is used for each of the sites serving as an imaging target. In this situation, the exclusive-use coil may be, for example, a receiving coil for the head, a receiving coil for the spine, or a receiving coil for the abdomen.

The receiver 9 is configured to generate MR signal data on the basis of the MR signals received by the receiving coil 8. More specifically, the receiver 9 generates the MR signal data by applying a digital conversion to the MR signals and transmits the generated MR signal data to the acquiring unit 11.

In the following sections, an example will be explained in which the transmitting coil 6 applies the RF magnetic field, whereas the receiving coil 8 receives the MR signals; however, possible embodiments are not limited to this example. For instance, the transmitting coil 6 may further have a receiving function of receiving the MR signals, or the receiving coil 8 may further have a transmitting function of applying the RF magnetic field. If the transmitting coil 6 has the receiving function, the receiver 9 generates MR signal data also from the MR signals received by the transmitting coil 6. Further, if the receiving coil 8 has the transmitting function, the transmitter 7 supplies the RF pulse current also to the receiving coil 8.

The sequence controller 10 is configured to execute various types of pulse sequences. More specifically, the sequence controller 10 executes the various types of pulse sequences by driving the gradient power source 3, the transmitter 7, and the receiver 9, on the basis of sequence execution data transmitted thereto from a host controller 24. In this situation, the sequence execution data is information defining a pulse sequence that indicates a procedure for acquiring the MR signal data. More specifically, the sequence execution data is the information defining the timing with which the electric current is supplied by the gradient power source 3 to the gradient coil 2, the intensity of the supplied electric current, the timing with which the RF transmission from the transmitter 7 to the transmitting coil 6 is performed, the intensity of the transmitted RF pulse current, and the timing with which the MR signals are detected by the receiver 9.

As a result of the execution of any of the various types of pulse sequences, the acquiring unit 11 is configured to acquire the MR signal data generated by the receiver 9. More specifically, when having received the MR signal data from the receiver 9, the acquiring unit 11 performs a correcting process such as an averaging process and/or a phase correcting process on the received MR signal data, and transmits the corrected MR signal data to the image generator 12. Further, the acquiring unit 11 transmits the data of the acquired images to the host computer 20. A set made up of the pieces of MR signal data acquired by the acquiring unit 11 is stored as data structuring a k-space in a storage 21 of the host computer 20, as a result of the pieces of MR data being arranged in a two- or three-dimensional formation in accordance with the position information appended thereto by the read-out gradient magnetic field, the phase-encoding gradient magnetic field, and the slice gradient magnetic field.

The image generator 12 is configured to generate images on the basis of the MR signal data acquired by the acquiring unit 11. More specifically, when having received the MR signal data from the acquiring unit 11, the image generator 12 generates the images of the patient S, by performing a post-processing process, i.e., a reconstructing process such as a Fourier transformation on the received MR signal data. Further, the image generator 12 transmits the data of the generated images to the host computer 20.

The host computer 20 is configured to exercise overall control of the MRI apparatus 100. For example, the host computer 20 includes the storage 21, an operating unit 22, a display 23, and the host controller 24.

The storage 21 is configured to store therein various types of data. For example, the storage 21 stores therein the MR signal data acquired by the sequence controller 10 and the data of the images generated by the image generator 12 for each patient S. Further, the storage 21 is configured to store therein various types of computer programs and various types of data that are used by the host controller 24 when performing various types of processes.

The operating unit 22 is configured to receive inputs of various types of instructions and various types of information from an operator of the apparatus. For example, the operating unit 22 receives an input of imaging conditions from the operator.

The display 23 is configured to display various types of information and various types of images. For example, the display 23 displays a Graphical User Interface (GUI) used for receiving the inputs of the various types of instructions and the various types of information from the operator. Further, for example, the display 23 displays the images generated by the image generator 12.

The host controller 24 is configured to exercise overall control of the MRI apparatus 100, by controlling the functional elements included in the MRI apparatus 100. For example, the host controller 24 receives an input of various types of imaging parameters from the operator via the operating unit 22 and sets the imaging conditions on the basis of the received imaging parameters. More specifically, the host controller 24 includes a setting unit 24a. For example, the setting unit 24a is configured to cause the display 23 to display a GUI used for receiving the input of the various types of imaging parameters from the operator and to set the imaging conditions on the basis of the various types of imaging parameters that were input via the GUI.

Further, for example, the host controller 24 operates the couch 4, by controlling the couch controller 5 on the basis of an instruction received from the operator via the operating unit 22. Further, the host controller 24 executes the various types of pulse sequences by generating the sequence execution data on the basis of the imaging conditions and transmitting the generated sequence execution data to the sequence controller 10. Further, the host controller 24 stores the MR signal data transmitted thereto from the acquiring unit 11 and the data of the images transmitted thereto from the image generator 12 as a result of executing the pulse sequence, into the storage 21. Further, the host controller 24 reads any of the images requested by the operator from the storage 21 and outputs the read image to the display 23.

Of the functional elements described above, the sequence controller 10, the acquiring unit 11, the image generator 12, and the host controller 24 are, for example, configured with processing circuitry such as a processor such as a Central Processing Unit (CPU) or a Micro Processing Unit (MPU); a memory; an Application Specific Integrated Circuit (ASIC); or a Field Programmable Gate Array (FPGA). Further, for example, the storage 21 is configured with a storage device such as a Random Access Memory (RAM), a Read-Only Memory (ROM), a flash memory, a hard disk, or an optical disk. Further, for example, the operating unit 22 is configured with an input device such as a keyboard, a mouse, a trackball, a touch panel, a button, a switch, and/or the like. Further, for example, the display 23 is configured with a display device such as a liquid crystal monitor, a Cathode-Ray Tube (CRT) monitor, a touch panel, or the like.

The configuration of the MRI apparatus 100 according to the present embodiment has thus been explained. The MRI apparatus 100 configured as described above has a function of acquiring images of a plurality of slice regions that are sequentially arranged. In the following sections, the process of acquiring the images of the plurality of slice regions that are sequentially arranged will be referred to as a multi slice imaging process. Further, in the following sections, a region that collectively encloses therein the plurality of slice regions of which the images are acquired in the multi slice imaging process will be referred to as a slab.

In this situation, when the multi slice imaging process is performed, in some situations, pre-sat pulses to make fluid signals void may be applied for the purpose of inhibiting flow artifacts caused by fluids such as blood and cerebrospinal fluid flowing into the slice regions. In those situations, the pre-sat pulses are applied to the outside of the slab so as not to influence the MR signals acquired from the slice regions.

Figure 2:
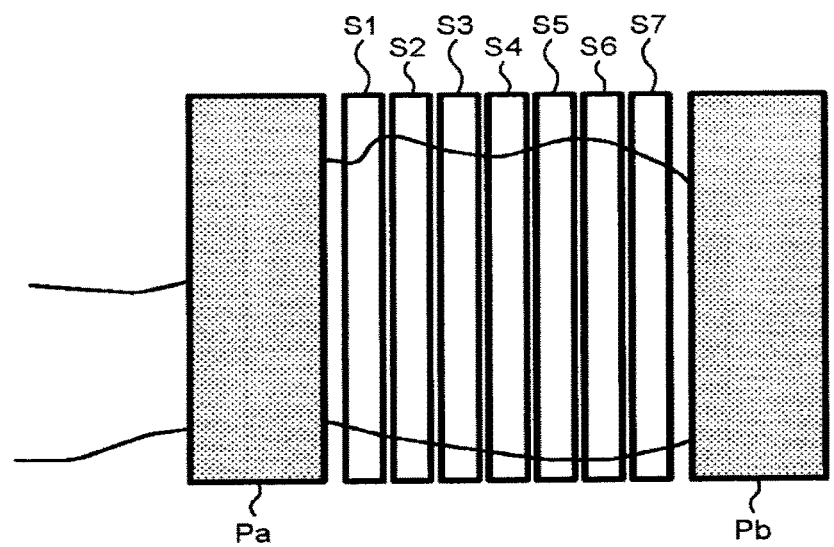
FIG. 2 is a drawing of an example of applications of pre-sat pulses during a multi slice imaging process.

FIG. 2 is a drawing of an example of the applications of the pre-sat pulses during the illustrated multi slice imaging process. FIG. 2 illustrates an example in which seven images are acquired on axial cross-sectional planes of the head. In FIG. 2, S1 to S7 denote the first to the seventh slice regions, respectively. Further, Pa and Pb each denote a pre-sat pulse application region.

In this situation, generally speaking, for multi slice imaging processes, the interval between the slices is arranged to be approximately 20% of the slice thickness. Typically, when the slice thickness is 5 mm, the slice interval is arranged to be 1 mm. For this reason, it is difficult to apply a pre-sat pulse to a position between the slice regions. Accordingly, as illustrated in FIG. 2, for example, the pre-sat pulses are applied to either side of the slab.

Figure 3:
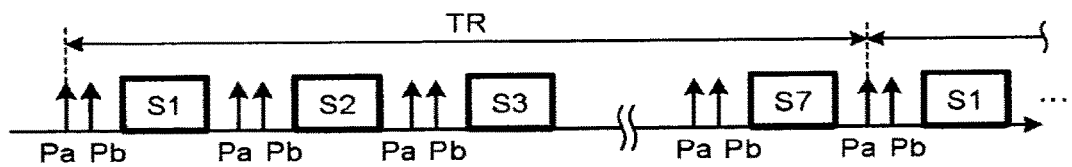
FIG. 3 is a drawing of an example of a pulse sequence executed during the illustrated multi slice imaging process.

FIG. 3 is a drawing of an example of a pulse sequence executed during the illustrated multi slice imaging process. In FIG. 3, S1 to S7 (S4 to S6 are omitted) denote imaging sections corresponding to the slice regions S1 to S7 illustrated in FIG. 2, respectively. In this situation, for example, in the imaging sections S1 to S7, images are acquired by implementing an arbitrary imaging method such as a spin echo method, a fast spin echo method, a gradient echo method, an Echo Planar Imaging (EPI) method, or the like.

In FIG. 3, Pa and Pb denote pre-sat pulses corresponding to the application regions Pa and Pb illustrated in FIG. 2, respectively. Further, as illustrated in FIG. 3, the pre-sat pulses Pa and Pb are applied immediately prior to each of the imaging sections S1 to S7. As a result, the application regions Pa and Pb that are set on either side of the slab collectively enclosing the slice regions S1 to S7 therein are excited.

Figure 4:
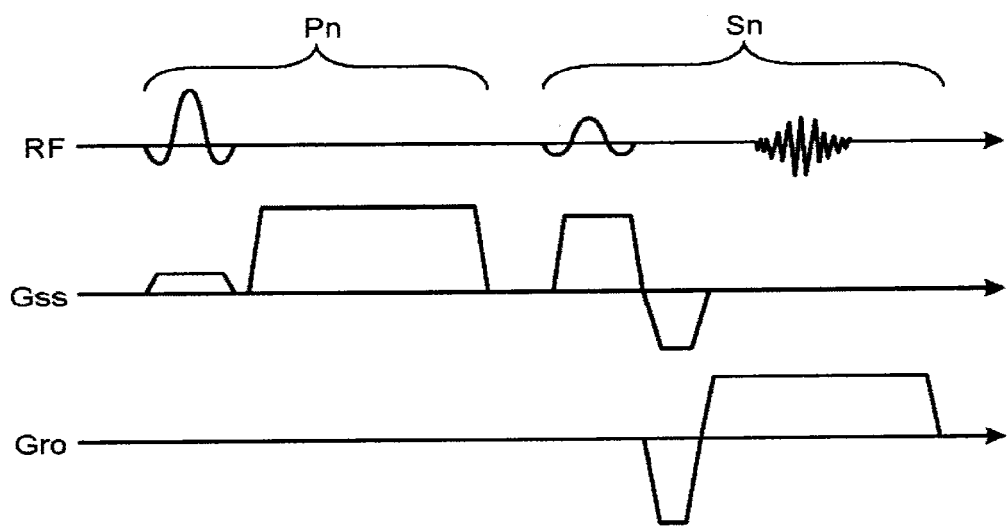
FIG. 4 is a drawing of an exemplary structure of each of the pre-sat pulses used in the illustrated multi slice imaging process.

FIG. 4 is a drawing of an exemplary structure of each of the pre-sat pulses used in the illustrated multi slice imaging process. In FIG. 4, Pn denotes a section (hereinafter, "pre-sat pulse section") in which a pre-sat pulse is applied. Sn denotes an imaging section. For the sake of convenience in the explanation, FIG. 4 illustrates only one pre-sat pulse section and one imaging section. However, the pre-sat pulse section Pn may be either of the pre-sat pulses Pa and Pb illustrated in FIG. 3. The imaging section Sn may be any of the imaging sections S1 to S7 illustrated in FIG. 3.

For example, as illustrated in FIG. 4, the pre-sat pulse section Pn is structured so as to include a 90-degree pulse, which is an RF pulse of which the flip angle is 90 degrees, and a spoiler gradient magnetic field that is applied immediately after the 90-degree pulse. In this situation, for example, the spoiler gradient magnetic field is applied in the slice direction so as to disperse the phase of a transverse magnetization of a spin.

Further, during the multi slice imaging process, the data acquisition from each of the slice regions S1 to S7 is repeatedly performed at time intervals of TR (Repetition Time), while varying the intensity of the phase-encoding gradient magnetic field for each of the imaging sections S1 to S7, until the data required by the generation of the image of each of the slice regions is acquired.

In this situation, as explained above, during the multi slice imaging process, the pre-sat pulses are applied to the outside of the slab collectively enclosing the plurality of slice regions therein. However, as illustrated in FIG. 3, for example, during the multi slice imaging process, because the data is acquired from each of the slice regions, there is a distance corresponding to one or more other slice regions between the position where the pre-sat pulse is applied and the position of each slice region. As a result, flow artifacts may be caused by fluid flowing therein from a region to which the pre-sat pulse is not applied and which includes one or more closely-positioned slice regions. Thus, there may be some situations where it is not possible to sufficiently inhibit the flow artifacts.

For this reason, in the present embodiment, when a multi slice imaging process is performed, the sequence controller 10 is configured to divide the plurality of slice regions that are sequentially arranged into a first group including two non-sequential slice regions and a second group including a slice region positioned between the two non-sequential slice regions and to acquire data from the slice regions for each of the groups. In the following sections, each of the groups into which the slice regions are divided will be referred to as a "coverage group".

Further, in the present embodiment, when acquiring data from the slice regions in the first group, the sequence controller 10 acquires data from at least one of the two non-sequential slice regions, after applying a pre-sat pulse to a position between the two non-sequential slice regions. In contrast, when acquiring data from the slice region included in the second group, the sequence controller 10 acquires data from the slice region positioned between the two non-sequential slice regions, after applying a pre-sat pulse to a position of at least one of the two non-sequential slice regions.

With this arrangement, when the multi slice imaging process is performed, the pre-sat pulses are applied to the positions close to the slice regions. Consequently, it is possible to inhibit, with higher certainty, the flow artifacts that may be caused by the fluids flowing into the slice regions.

The multi slice imaging process according to the present embodiment will be explained in detail below. In the following sections, an example will be explained in which, similarly to the example illustrated in FIG. 2, images of the slice regions S1 to S7 are to be acquired on the axial cross-sectional planes of the head. For example, the multi slice imaging process described below is used when acquiring images of the cervical vertebrae. Further, in the following sections, an example will be explained in which the images are acquired by dividing the slice regions S1 to S7 into a first coverage group including slice regions corresponding to odd ordinal numbers and a second coverage group including slice regions corresponding to even ordinal numbers. In the following explanation, for the sake of convenience in the explanation, the direction from the center of the slab collectively enclosing the slice regions S1 to S7 therein, toward the slice region S1 will be referred to as a forward direction, whereas the direction toward the slice region S7 will be referred to as a backward direction.

Figure 5:
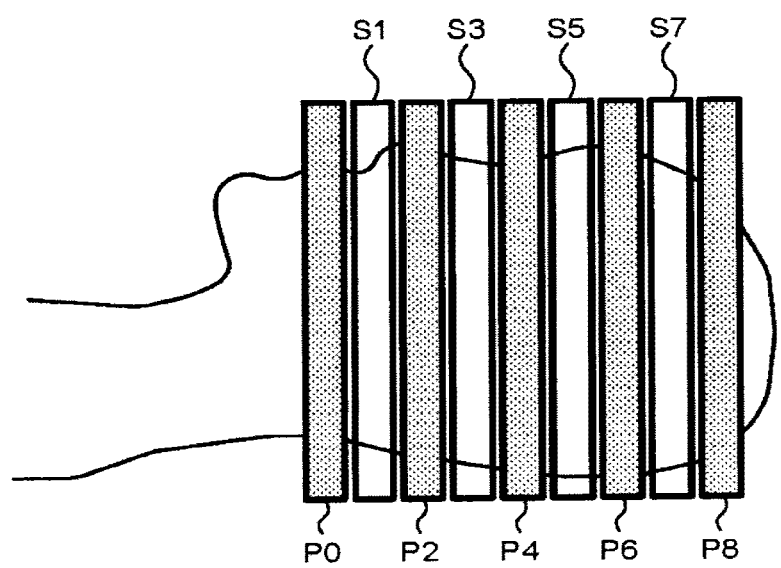
FIG. 5 is a drawing of an imaging process performed on a first coverage group in a multi slice imaging process according to the embodiment.

FIG. 5 is a drawing of an imaging process performed on the first coverage group in a multi slice imaging process according to the present embodiment. For example, as illustrated in FIG. 5, the sequence controller 10 acquires data from the slice regions S1, S3, S5, and S7 serving as the first coverage group.

In this situation, when acquiring the data from the slice region S1, the sequence controller 10 acquires the data after applying a pre-sat pulse P0 to the vicinity of the front side of the slice region S1 and applying a pre-sat pulse P2 to the position of the slice region S2. Further, when acquiring the data from the slice region S3, the sequence controller 10 acquires the data after applying a pre-sat pulse P2 to the position of the slice region S2 and applying a pre-sat pulse P4 to the position of the slice region S4. Further, when acquiring the data from the slice region S5, the sequence controller 10 acquires the data after applying a pre-sat pulse P4 to the position of the slice region S4 and applying a pre-sat pulse P6 to the position of the slice region S6. Further, when acquiring the data from the slice region S7, the sequence controller 10 acquires the data after applying a pre-sat pulse P6 to the position of the slice region S6 and applying a pre-sat pulse P8 to the vicinity of the back side of the slice region S7. The thickness of each of the application regions of the pre-sat pulses P0, P2, P4, P6, and P8 in the slice direction is configured to be, for example, equal to the thickness of each of the slice regions.

Figure 6:
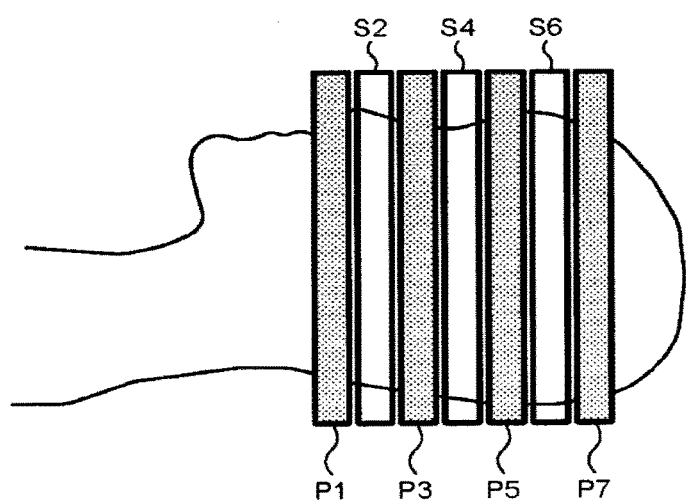
FIG. 6 is a drawing of an imaging process performed on a second coverage group in the multi slice imaging process according to the embodiment.

FIG. 6 is a drawing of an imaging process performed on the second coverage group in a multi slice imaging process according to the present embodiment. For example, as illustrated in FIG. 6, the sequence controller 10 acquires the data from the slice regions S2, S4, and S6 serving as the second coverage group.

In this situation, when acquiring the data from the slice region S2, the sequence controller 10 acquires the data after applying a pre-sat pulse P1 to the position of the slice region S1 and applying a pre-sat pulse P3 to the position of the slice region S3. Further, when acquiring the data from the slice region S4, the sequence controller 10 acquires the data after applying a pre-sat pulse P3 to the position of the slice region S3 and applying a pre-sat pulse P5 to the position of the slice region S5. Further, when acquiring the data from the slice region S6, the sequence controller 10 acquires the data after applying a pre-sat pulse P5 to the position of the slice region S5 and applying a pre-sat pulse P7 to the position of the slice region S7. The thickness of each of the application regions of the pre-sat pulses P1, P3, P5, and P7 in the slice direction is configured to be, for example, equal to the thickness of each of the slice regions.

As explained above, in the multi slice imaging process according to the present embodiment, to acquire the data from each of the slice regions in each of the coverage groups, the sequence controller 10 applies each of the pre-sat pulses to the position between the slice position and the adjacently-positioned slice region. Further, for example, to acquire the data from the slice region S1, the sequence controller 10 applies the pre-sat pulses P0 and P2 to the front and the back of the slice region S1. To acquire the data from the slice region S2, the sequence controller 10 applies the pre-sat pulses P2 and P4 to the front and the back of the slice region S3. In this manner, in each of the coverage groups, the sequence controller 10 uses mutually the same pre-sat pulse for the two slice regions that are positioned adjacent to each other.

Figure 7:
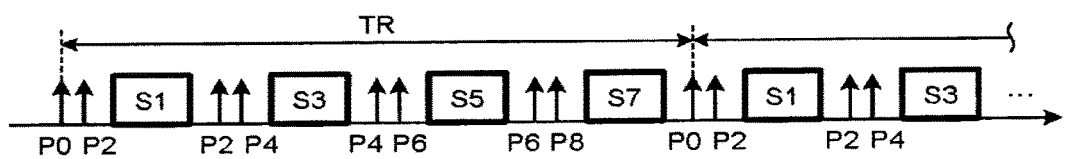
FIG. 7 is a drawing of an example of a pulse sequence executed on the first coverage group according to the embodiment.

FIG. 7 is a drawing of an example of a pulse sequence executed on the first coverage group according to the present embodiment. In FIG. 7, S1, S3, S5, and S7 denote imaging sections corresponding to the slice regions illustrated in FIG. 5. In this situation, similarly to the example illustrated in FIG. 3, in the imaging sections S1, S3, S5, and S7, images are acquired by using an arbitrary imaging method such as, for example, a spin echo method, a fast spin echo method, a gradient echo method, an EPI method, or the like.

Further, in FIG. 7, P0, P2, P4, P6, and P8 denote pre-sat pulses corresponding to the application regions P0, P2, P4, P6, and P8 illustrated in FIG. 5. In this situation, as each of the pre-sat pulses P0, P2, P4, P6, and P8, for example, an equivalent of the pre-sat pulse section Pn illustrated in FIG. 4 is used. Further, as illustrated in FIG. 7, the pre-sat pulses P0 and P2 are applied immediately prior to the imaging section S1, whereas the pre-sat pulses P2 and P4 are applied immediately prior to the imaging section S3. Further, the pre-sat pulses P4 and P6 are applied immediately prior to the imaging section S5, whereas the pre-sat pulses P6 and P8 are applied immediately prior to the imaging section S7. As a result, the application regions that are set in the positions adjacent to each of the slice regions S1, S3, S5, and S7 are excited.

As for the first coverage group, the data acquisition from each of the slice regions S1, S3, S5, and S7 is repeatedly performed at the time intervals of TR, while varying the intensity of the phase-encoding gradient magnetic field for each of the imaging sections S1, S3, S5, and S7, until the data required by the generation of the image of each of the slice regions is acquired.

Figure 8:
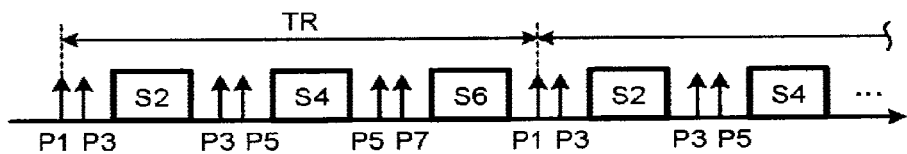
FIG. 8 is a drawing of an example of a pulse sequence executed on the second coverage group according to the embodiment.

FIG. 8 is a drawing of an example of a pulse sequence executed on the second coverage group according to the present embodiment. In FIG. 8, S2, S4, and S6 denote imaging sections corresponding to the slice regions illustrated in FIG. 6. In this situation, similarly to the example illustrated in FIG. 3, in the imaging sections S2, S4, and S6, images are acquired by using an arbitrary imaging method such as, for example, a spin echo method, a fast spin echo method, a gradient echo method, an EPI method, or the like.

Further, in FIG. 8, P1, P3, P5, and P7 denote pre-sat pulses corresponding to the application regions P1, P3, P5, and P7 illustrated in FIG. 6. In this situation, as each of the pre-sat pulses P1, P3, P5, and P7, for example, an equivalent of the pre-sat pulse section Pn illustrated in FIG. 4 is used. Further, as illustrated in FIG. 8, the pre-sat pulses P1 and P3 are applied immediately prior to the imaging section S2, whereas the pre-sat pulses P3 and P5 are applied immediately prior to the imaging section S4, and the pre-sat pulses P5 and P7 are applied immediately prior to the imaging section S6. As a result, the application regions that are set in the positions adjacent to each of the slice regions S2, S4, and S6 are excited.

As for the second coverage group, the data acquisition from each of the slice regions S2, S4, and S6 is repeatedly performed at the time intervals of TR, while varying the intensity of the phase-encoding gradient magnetic field for each of the imaging sections S2, S4, and S6, until the data required by the generation of the image of each of the slice regions is acquired.

As explained above, in the multi slice imaging process according to the present embodiment, for each of the coverage groups, the pre-sat pulses are applied to the close positions in the front and the back of each of the slice regions. With this arrangement, it is possible to reduce, with higher certainty, the flow artifacts caused by fluids flowing in the slice direction.

Figure 9:
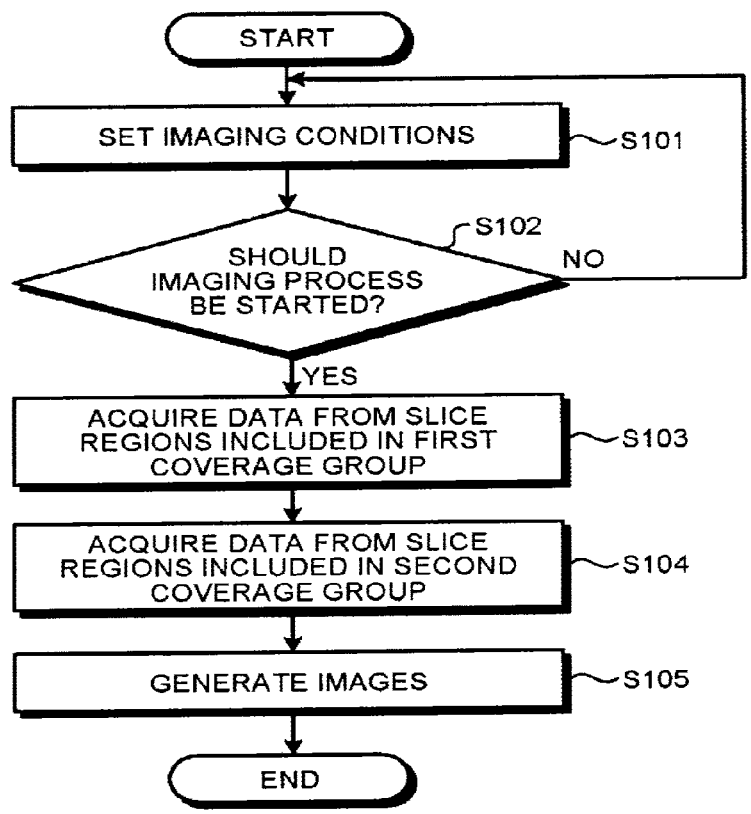
FIG. 9 is a flowchart of a processing procedure in a multi slice imaging process performed by the MRI apparatus according to the embodiment.

FIG. 9 is a flowchart of a processing procedure in the multi slice imaging process performed by the MRI apparatus 100 according to the present embodiment. As illustrated in FIG. 9, in the MRI apparatus 100, the setting unit 24a, at first, sets imaging conditions of the multi slice imaging process (step S101). In this situation, the setting unit 24a receives, as one of the imaging parameters, the quantity of coverage groups that is used when dividing the plurality of slice regions into a plurality of coverage groups.

After that, when having received an instruction to start an imaging process from the operator (step S102: Yes), the host controller 24 generates sequence execution data on the basis of the imaging conditions set by the setting unit 24a and transmits the generated sequence execution data to the sequence controller 10. In that situation, the host controller 24 generates the sequence execution data for acquiring images by dividing the plurality of slice regions into the coverage groups of which the quantity was set by the operator and transmits the generated sequence execution data to the sequence controller 10.

After that, the sequence controller 10 sequentially acquires data from the plurality of slice regions for each of the coverage groups. For example, the sequence controller 10 acquires the data from the slice regions included in the first coverage group (step S103). Further, the sequence controller 10 acquires the data from the slice regions included in the second coverage group (step S104). After that, the image generator 12 generates images of the plurality of slice regions, on the basis of the data acquired by the sequence controller 10 (step S105).

In the explanation above, the example is explained in which the sequence controller 10 acquires the data from the first coverage group including the slice regions corresponding to the odd ordinal numbers and from the second coverage group including the slice regions corresponding to the even ordinal numbers, in the stated order; however, the order in which the data is acquired from each of the coverage groups is not limited to this example. For instance, the sequence controller 10 may acquire the data from the second coverage group including the slice regions corresponding to the even ordinal numbers and from the first coverage group including the slice regions corresponding to the odd ordinal numbers, in the stated order.

As explained above, according to the present embodiment, when performing the multi slice imaging process, the sequence controller 10 divides the plurality of slice regions that are sequentially arranged, into the first coverage group including the two non-sequential slice regions and the second coverage group including the slice region positioned between the two non-sequential slice regions and further acquires the data from the slice regions for each of the coverage groups. Further, when acquiring the data from the slice regions included in the first group, the sequence controller 10 acquires the data from at least one of the two non-sequential slice regions after applying the pre-sat pulse to the position between the two non-sequential slice regions. In contrast, when acquiring the data from the slice region included in the second group, the sequence controller 10 acquires the data from the slice region positioned between the two non-sequential slice regions after applying the pre-sat pulse to the position of at least one of the two non-sequential slice regions. After that, the image generator 12 generates the images of the plurality of slice regions, on the basis of the data acquired by the sequence controller 10.

In other words, the sequence controller 10 divides the plurality of slice regions included in the multi slice imaging process into the first group including the two slice regions that are not positioned adjacent to each other and the second group including the slice region interposed between the two slice regions and further acquires the data from the slice regions included in the first group and the data from the slice region included in the second group. In that situation, when acquiring the data from the first group, the sequence controller 10 acquires the data after applying the pre-sat pulse to the position of the slice region that is interposed between the two slice regions and is included in the second group. When acquiring the data from the second group, the sequence controller 10 acquires the data after applying the pre-sat pulse to the position of at least one of the two slice regions. After that, the image generator 12 generates the images of the plurality of slice regions, on the basis of the data acquired by the sequence controller 10.

With this arrangement, when the multi slice imaging process is performed, the pre-sat pulses are applied to the positions close to the slice regions, for each of the coverage groups. Consequently, according to the present embodiment, it is possible to inhibit, with higher certainty, the flow artifacts that are caused by the fluids flowing into the slice regions.

The MRI apparatus 100 according to the present embodiment has thus been explained. However, possible embodiments of the present disclosure are not limited to those described above. It is possible to partially apply various modifications to the configurations.

For example, in the embodiment described above, the example is explained in which, as illustrated in FIGS. 5 and 6, the pre-sat pulses are applied to the front and the back of each of the slice regions for each of the coverage groups. However, possible embodiments are not limited to this example. For instance, if one of the fluids flowing into a slice region from the front and from the back has a relatively low flow rate or a relatively small flow amount, the flow artifact caused by such a fluid may be negligible.

In that situation, for example, the sequence controller 10 may apply, in each of the coverage groups, a pre-sat pulse only to one of the front and back sides of each of the slice regions, i.e., only for the one of the fluids of which the flow artifact is not negligible. By limiting the position to which the pre-sat pulse is applied to only one of the front and the back of each of the slice regions, it is possible to reduce the number of times the pre-sat pulse is applied, and it is therefore possible to shorten the time period required by the multi slice imaging process.

In that situation, for example, when setting the imaging conditions, the setting unit 24a receives information about the positions to which the pre-sat pulses are to be applied from the operator, as one of the imaging parameters. For example, the setting unit 24a receives an operation to select one from among "front", "back", "front and back", from the operator, as the information about the positions to which the pre-sat pulses are to be applied.

Further, for example, as a part of functions to aid an imaging planning process performed by a medical doctor, a medical technician, or the like, the MRI apparatus 100 may manage and provide information about a pulse sequence in which specific imaging parameter values are set in advance, as protocol information. For example, in accordance with the type or the purpose of a medical examination, a plurality of pieces of protocol information are prepared for each imaging target site. In that situation, the operator such as a medical doctor, a medical technician, or the like sets the imaging conditions by selecting a piece of protocol information, as appropriate, from among the group of pieces of protocol information managed and provided by the MRI apparatus 100 and correcting any of the imaging parameter values as necessary. In that situation, for example, the MRI apparatus 100 may be configured so as to manage the quantity of coverage groups and/or the positions in which the pre-sat pulses are to be applied, as a part of the protocol information.

Further, in the embodiment described above, the example is explained in which the images are acquired by dividing the plurality of slice regions into the two coverage groups. However, possible embodiments are not limited to this example. For instance, the quantity of coverage groups may be three or more. When the images are acquired by dividing the plurality of slice regions into a plurality of groups in this manner, the larger the quantity of coverage groups is, the larger the interval between the slice regions is in each of the coverage groups.

For this reason, the sequence controller 10 may arrange the pre-sat pulse application regions in each of the groups in such a manner that the larger the quantity of coverage groups is, the larger each of the pre-sat pulse application regions is. For example, the sequence controller 10 sets the size of the pre-sat pulse application regions in accordance with the interval between the slice regions in each of the coverage groups. In that situation, the sequence controller 10 ensures that there is a predetermined interval between each of the pre-sat pulse application regions and the corresponding slice region in such a manner that the impact made on the slice region by the excitation caused by the pre-sat pulse is within a tolerable range.

For example, when the slice thickness is 5 mm, while the slice interval is 1 mm, if the quantity of coverage groups is two, the interval between the slice regions is 7 mm, to leave the space corresponding to one slice region. In that situation, for example, the sequence controller 10 sets the width of each of the pre-sat pulse application regions in the slice direction to 6 mm. In another example, if the quantity of coverage groups is three, for instance, the interval between the slice regions is 13 mm, to leave the space corresponding to two slice regions. In that situation, for example, the sequence controller 10 sets the width of each of the pre-sat pulse application regions in the slice direction to 12 mm. In these examples, the interval between each of the pre-sat pulse application regions and the corresponding slice region is 0.5 mm.

Further, in the embodiment described above, the example is explained in which, for each of the coverage groups, the pre-sat pulses are applied to either side of a slice region and the position between a slice region and the adjacently-positioned slice region; however, possible embodiments are not limited to this example. For instance, the sequence controller 10 may acquire the data from the slice regions, by further applying pre-sat pulses to the outside of the slab that collectively encloses the plurality of slice regions therein.

For example, to acquire the data from the first coverage group, the sequence controller 10 acquires the data from the slice regions S1, S3, S5, and S7, by further applying the pre-sat pulses Pa and Pb illustrated in FIG. 2, in addition to the pre-sat pulses P0, P2, P4, P6, and P8 illustrated in FIG. 5. Further, for example, to acquire the data from the second coverage group, the sequence controller 10 acquires the data from the slice regions S2, S4, and S6, by further applying the pre-sat pulses Pa and Pb illustrated in FIG. 2, in addition to the pre-sat pulses P1, P3, P5, and P7 illustrated in FIG. 6.

By further applying the pre-sat pulses to the outside of the slab in this manner, in addition to the pre-sat pulses applied to the vicinity of the slice regions, it is possible to reduce both the flow artifacts caused by fluids flowing into the slice regions from farther positions and the flow artifacts caused by fluids flowing into the slice regions from closer positions. Consequently, it is possible to inhibit, with even higher certainty, the flow artifacts that are caused in the slice regions.

In the embodiment described above, the example is explained in which the images of every other slice region are acquired in each of the coverage groups, by dividing the plurality of slice regions into the first coverage group including the slice regions corresponding to the odd ordinal numbers and the second coverage group including the slice regions corresponding to the even ordinal numbers; however, possible embodiments are not limited to this example. For instance, the sequence controller 10 may set the coverage groups so that, when the images of the plurality of slice regions are acquired in divided groups, images of one in every three or more slice regions are acquired.

For example, when acquiring the images of the slice regions S1 to S7 similarly to the example illustrated in FIG. 2, the sequence controller 10 acquires the data from the slice regions by dividing the slice regions into a coverage group including the slice regions S1, S2, S5, and S6 and another coverage group including the slice regions S3, S4, and S7. In that situation, the thickness of each of the pre-sat pulse application regions in the slice direction may be equal to the thickness of each of the slice regions or may be the maximum thickness that keeps the impact made on the slice regions by the excitation caused by the pre-sat pulses in a tolerable range.

When the images are acquired by dividing the slice regions into the groups while using one in every three or more slice regions in this manner, when the data is acquired from each of the slice regions, lies between the pre-sat pulse and the slice region is a distance corresponding to the slice region positioned adjacent thereto. However, the distance in this situation is shorter than the distance at which the pre-sat pulses are each applied to the outside of the slab. Consequently, compared to the situation where the pre-sat pulses are applied to the outside of the slab, it is possible to reduce the flow artifacts.

Further, in the embodiment described above, the example is explained in which, when setting the imaging conditions, the setting unit 24a causes the display 23 to display the GUI used for receiving the input of the various types of imaging parameters from the operator; however, possible embodiments are not limited to this example. For instance, the setting unit 24a may cause the display 23 to display information indicating the positions to which the pre-sat pulses are to be applied, together with the GUI.

For example, when the images are acquired by dividing the plurality of slice regions into a plurality of coverage groups, the setting unit 24a causes information to be displayed so as to indicate the positions to which the pre-sat pulses are to be applied, for each of the coverage groups.

In a specific example, for instance, as for the first coverage group, the setting unit 24a causes the information S1, S3, S5, and S7 indicating the positions of the slice regions of which the images are acquired in the first coverage group and the information P0, P2, P4, P6, and P8 indicating the positions of the pre-sat pulse application regions used for the first coverage group to be displayed as being superimposed on the information indicating the patient, as illustrated in FIG. 5. Further, for example, as for the second coverage group, the setting unit 24a causes the information S2, S4, and S6 indicating the positions of the slice regions of which the images are acquired in the second coverage group and the information P1, P3, P5, and P7 indicating the positions of the pre-sat pulse application regions used for the second coverage group to be displayed as being superimposed on the information indicating the patient, as illustrated in FIG. 6. In this situation, as the information indicating the patient, for example, the setting unit 24a displays an image of the patient (e.g., an image acquired during a position determining process, an image acquired by a protocol at a previous stage, or the like) or a graphic element that schematically expresses the body shape of the patient. Further, as the information indicating the slice regions and the information indicating the pre-sat pulse application regions, the setting unit 24a displays, for example, rectangular graphic elements and/or linear graphic elements. For example, the setting unit 24a displays the graphic elements expressing the slice regions and the graphic elements expressing the pre-sat pulse application regions, while varying the display modes thereof (e.g., the shapes, the colors, the patterns, etc.).

Further, for example, instead of displaying the information indicating the positions to which the pre-sat pulses are to be applied for each of the coverage groups separately, the setting unit 24a may display information indicating that the pre-sat pulses are to be applied to the front of the slice regions, that the pre-sat pulses are to be applied to the back of the slice regions, or that the pre-sat pulses are to be applied to the front and the back of the slice regions, as information that is common to all the coverage groups.

In a specific example, for instance, the setting unit 24a causes the information S1 to S7 indicating the positions of the slice regions as well as the information Pa indicating the pre-sat pulse applied to the front side and the information Pb indicating the pre-sat pulse applied to the back side to be displayed as being superimposed on the information indicating the patient, as illustrated in FIG. 2. In this situation, the setting unit 24a displays only the information Pa, when the pre-sat pulses are applied to the front side of the slice regions for each of the coverage groups. In another situation, the setting unit 24a displays only the information Pb, when the pre-sat pulses are applied to the back side of the slice regions for each of the coverage groups. In yet another situation, the setting unit 24a displays both the information Pa and the information Pb, when the pre-sat pulses are applied to the front and the back of the slice regions for each of the coverage groups.

Further, in the embodiment described above, the example is explained in which the quantity of coverage groups is received from the operator, as one of the imaging parameters. However, possible embodiments are not limited to this example. For instance, the setting unit 24a may automatically calculate the quantity of coverage groups, on the basis of a TR value and the quantity of slices that are input as imaging parameters. In that situation, the setting unit 24a, at first, calculates the quantity of slices of which it is possible to acquire images within the input TR. After that, the setting unit 24a calculates the quantity of coverage groups required to acquire the images of the slice regions corresponding to the quantity of slices that was input, by dividing the quantity of slices that was input by the quantity of slices that was calculated on the basis of the TR. Further, the setting unit 24a may further receive the quantity of slices of which the images are to be acquired in a single coverage group, from the operator. In that situation, for example, the setting unit 24a calculates the quantity of coverage groups, in such a manner that the quantity of slices of which the images are acquired for each coverage group does not exceed the quantity of slices of which the images are acquired in the single coverage group.

According to at least one aspect of the embodiments described above, it is possible to inhibit the flow artifacts, with higher certainty.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
processing circuitry configured to
divide a plurality of slice regions sequentially arranged into a first group and a second group, and acquire data of the slice regions for each of the groups, the first group including two non-sequential slice regions, the second group including a slice region positioned between the two non-sequential slice regions; and
generate images of the plurality of slice regions on a basis of the acquired data, wherein
when acquiring data from at least one of the two non-sequential slice regions, the processing circuitry acquires the data after applying a pre-sat pulse to a position between the two non-sequential slice regions, and when acquiring data from the slice region positioned between the two non-sequential slice regions, the processing circuitry acquires the data after applying a pre-sat pulse to a position of at least one of the two non-sequential slice regions.

2. The magnetic resonance imaging apparatus according to claim 1, wherein the processing circuitry acquires the data from the plurality of slice regions divided into a plurality of groups, and wherein the processing circuitry sets pre-sat pulse application regions in each of the groups in such a manner that the larger a value indicating a quantity of groups is, the larger each of the pre-sat pulse application regions is.

3. The magnetic resonance imaging apparatus according to claim 1, wherein the processing circuitry acquires the data from the plurality of slice regions after further applying a pre-sat pulse to an outside of a region that collectively encloses the plurality of slice regions therein.

4. The magnetic resonance imaging apparatus according to claim 1, wherein the processing circuitry is further configured to set an imaging condition, and wherein when setting the imaging condition, the processing circuitry causes a display to display information indicating positions to which the pre-sat pulses are to be applied.

5. The magnetic resonance imaging apparatus according to claim 4, wherein the processing circuitry causes the information indicating the positions to which the pre-sat pulses are to be applied, for each of the groups.

6. A magnetic resonance imaging apparatus comprising:
processing circuitry configured to divide a plurality of slice regions included in a multi slice imaging process into a first group and a second group, and acquire data of the slice regions included in the first group and data of the slice region included in the second group, the first group including two slice regions that are not positioned adjacent to each other, the second group including a slice region interposed between the two slice regions; and generate images of the plurality of slice regions on a basis of the acquired data, wherein when acquiring the data of the first group, the processing circuitry acquires the data after applying a pre-sat pulse to a position of the slice region that is interposed between the two slice regions and is included in the second group, and when acquiring the data of the second group, the processing circuitry acquires the data after applying a pre-sat pulse to a position of at least one of the two slice regions.

* * * * *

UNITED STATES PATENT AND TRADEMARK OFFICE
CERTIFICATE OF CORRECTION

| | | |
|---|---|---|
| PATENT NO. | : 9,770,187 B2 | Page 1 of 1 |
| APPLICATION NO. | : 14/861393 | |
| DATED | : September 26, 2017 | |
| INVENTOR(S) | : Masaaki Umeda et al. | |

It is certified that error appears in the above-identified patent and that said Letters Patent is hereby corrected as shown below:

On the Title Page

Item (30), the Foreign Application Priority Data Information is incorrect. Item (30) should read:
-- (30) Foreign Application Priority Data
Sep. 30, 2014   (JP)...........................2014-201910 --

Signed and Sealed this
Twenty-first Day of August, 2018

Andrei Iancu
*Director of the United States Patent and Trademark Office*